US006437158B1

(12) United States Patent
D. et al.

(10) Patent No.: US 6,437,158 B1
(45) Date of Patent: Aug. 20, 2002

(54) TESTOSTERONE DERIVATIVE

(75) Inventors: Dirk Leysen D., Lommel (BE);
Hendrikus Adrianus Antonius Van Der Voort H.A.A, Veghel (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/719,927

(22) PCT Filed: Jun. 14, 1999

(86) PCT No.: PCT/EP99/04102
§ 371 (c)(1),
(2), (4) Date: Dec. 18, 2000

(87) PCT Pub. No.: WO99/67271
PCT Pub. Date: Dec. 29, 1999

(30) Foreign Application Priority Data

Jun. 19, 1998 (EP) ............................................. 98202052

(51) Int. Cl.[7] .............................. C07J 1/00; A61K 31/56
(52) U.S. Cl. ....................... 552/623; 552/623; 552/632; 514/169; 514/182
(58) Field of Search ................................ 552/623, 632; 514/182

(56) References Cited

U.S. PATENT DOCUMENTS 5,342,834 A    8/1994   Bardin et al. ............... 514/178

OTHER PUBLICATIONS

Bremner, William J. et al. (DN 134:80878, Caplus, abstract of Int. Congr. Ser. (2000), 1206 (Current Knowledge in Reproductive Medicine), 315–331).*

Chaudry, M., et al., "Hansch analysis of the anabolic activites of some nandrolone esters" Journal of medical Chemistry, vol. 17, No. 2, Feb. 1974.

Kumar, N. et al. "Pharmacokinetics of 7 alpha–methyl–19–nortestosterone in men and cynomolgus monkeys" Chemical Abstracts, vol. 127, No. 18, Nov. 3, 1997.

Zhang, Y. et al., "Pharmacological studies of testosterone undecanoate, a new long–acting androgen preparation" Chemical Abstract, vol. 104, No. 9, Mar. 3, 1986.

Davidson, D. et al., "Increasing testosterone undecanoate in eugonadal men" Chemical Abstract, vol. 107, No. 13. Sep. 28, 1987.

* cited by examiner

*Primary Examiner*—Sabiha Qazi
(74) *Attorney, Agent, or Firm*—Mark W. Milstead

(57) ABSTRACT

The invention is drawn to (7a, 17b)-7-methyl-17-(1-oxoundecyl)oxy-estr-4-en-3-one, (MENT undecanoate), their pharmaceutical formulation and method of use is described. Unexpected results of the said compound compared with testosterone undecanoate is disclosed.

7 Claims, No Drawings

TESTOSTERONE DERIVATIVE

This application is a 371 of PCT/EP99/04102, filed on Jun. 14, 1999.

The invention is in the field of androgenic hormones, more specifically derivatives of testosterone.

Testosterone derivatives are known. Testosterone itself, the natural male hormone, has many known drawbacks as far as methods of administration are concerned. It has a short-lasting activity, is insoluble in the usual pharmaceutically acceptable media, and is not very potent. The more potent dihydrotestosterone (5α-reduced form of testosterone) is considered a health-risk, notably for the prostate. A somewhat better soluble derivative is testosterone undecanoate, which is known as the active substance in the product Andriol®.

More potent androgens are 7α-methyl-19-nortestosterone (MENT) and related compounds, such as disclosed in FR 4.521 M and U.S. Pat. No. 5,342,834. However, MENT suffers from a bad solubility and short duration of action.

New androgenic hormones are needed which inter alia satisfy the demands connected with new areas of interest, such as male contraception and male HRT (hormone replacement therapy). Thus, e.g., male contraception may comprise a regimen of administration of hormones in which a progestagen serves to achieve a contraceptive effect and an androgen serves to supplement the resulting decreased testosterone level. Another option is that male contraception is performed with an androgenic hormone alone. The regular androgen intake needed for this requires androgens which are improved as to potency and duration of action, and for which a practical way of administration is available. As low a frequency of administration being desired, there is a demand for androgens which have such physico-chemical properties as to be rendered into a solution, particularly a solution by which the androgen can be administered via injection, preferably once a week or less frequent, or orally via a capsule to be taken, e.g., daily. This means that a basic desired property for a novel androgen is that it has an improved solubility in one or more pharmaceutically acceptable liquids.

Even more desired is an androgen which has a favourable relationship of potency and solubility, as a weak androgen will require more of it to be dissolved in order to attain the same activity as a more potent androgen. This means an androgen having an improved relative "dissolved potency", hereinafter referred to as RDP, wherein the RDP of a given androgen in a given medium is the product of its androgenic potency relative to that of the natural male hormone testosterone and its solubility in the medium relative to that of testosterone.

It is an object of the invention to provide an androgenic hormone which satisfies the above demand. To this end, the invention is the compound (7α,17β)-7-methyl-17-[(1-oxoundecyl)oxy]estr-4-en-3-one, which has the following structural formula:

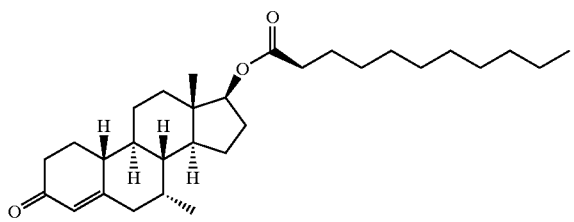

The compound of the invention is also to be referred to as 7α-methyl-19-nortestosterone undecanoate, in short MENT undecanoate.

The compound of the invention has a significantly better solubility than could be expected on the basis of the known testosterone derivatives. Moreover, the compound of the invention has a surprisingly higher RDP than the known compounds.

The compound of the invention can be prepared by esterification of the 17-OH group of MENT with undecanoic acid or derivatives thereof. This esterification may be carried out using methods well known in the art or readily available from the chemical literature, for example, using methods and catalysts described in Advanced Organic Chemistry, J. March, 4th Ed, pages 1281–1282, 1992. MENT can be prepared as disclosed in FR 4.521 M and U.S. Pat. No. 5,342,834.

The invention also pertains to the compound MENT undecanoate as a medicine. The compound of the invention being a potent androgen, it can be used in, inter alia, male contraception and male or female hormone replacement therapy. Thus the invention also pertains to a method of treatment of androgen insufficiency, by administering to a human male or female an effective amount of MENT undecanoate. The invention also is in the use of MENT undecanoate for the preparation of a medicine for treating androgen insufficiency. In the context of the invention, the term "androgen insufficiency" is to be understood to pertain to all kinds of diseases, disorders, and symptoms in which a male or a female suffers from too low a testosterone level, such as in hypogonadal men. In particular, the androgen insufficiency to be treated by the compound of the invention is the reduction of the testosterone level which a human male incurs as a result of age (the compound of the invention is then used for male hormone replacement therapy), or when he is subject to male contraception. In the context of male contraception, the compound of the invention especially serves to neutralise the effect of regimens of male hormone contraception in which a sterilitant such as a progestagen or LHRH (luteinizing hormone releasing hormone) is administered regularly, e.g. daily, or it is used as the sole male contraceptive substance.

The invention also relates to pharmaceutical formulations comprising MENT undecanoate and a pharmaceutically acceptable carrier. Thus the carrier may be in a solid form or liquid form, and the formulation may be an oral dosage unit such as a tablet or, preferably, an oral solution, e.g. in a capsule. Methods and compositions for making such dosage units are well-known to those skilled in the art. For example, conventional techniques for making tablets and pills, containing active ingredients, are described in the standard reference, Gennaro et al, Remington's Pharmaceutical Sciences, (18th ed., Mack Publishing Company, 1990, see especially Part 8: Pharmaceutical Preparations and Their Manufacture). The compound can also be administered via an implant, a patch, or any other suitable device for the sustained release of an androgen composition. The preferred oral dosage unit is that of a capsule containing the compound of the invention taken up in a liquid medium as described below.

In order to benefit most from the compound's androgenic activity, administration of the compound dissolved in an oil is preferred, i.e. either orally as above, and notably via (intramuscular) injection. MENT undecanoate has a solubility in oily media, which makes it particularly suitable for a liquid pharmaceutical formulation comprising MENT undecanoate dissolved in a pharmaceutically acceptable oil. Suitable oils are, e.g., arachis oil, oleic acid, ricinus oil, sesam oil and the like. Arachis oil is preferred.

For injection the preferred injection device is a needleless injection system, e.g. as described in U.S. Pat. No. 5,599,302. To this end the compound may also be suspended in an aqueous medium, but the above solutions in oil are preferred. Methods and compositions for making liquids suitable for parenteral administration are known in the art, see e.g. Remington's, pages 1545 ff.

For oral administration, any capsule made from a pharmaceutically acceptable wall material can be employed. Methods and compositions for making capsules suitable for oral administration are known in the art, see e.g. Remington's, pages 1658 ff. A preferred material is a softgel such as used for Andriol® capsules.

The invention also pertains to a method of treatment of androgen insufficiency, by administering to a human male, by injection or by means of an oral dosage unit, an effective amount of MENT undecanoate dissolved in a pharmaceutically acceptable oil. The invention also is in the use of MENT undecanoate for the preparation of a medicine for treating androgen insufficiency by injecting into a human male an effective amount of MENT undecanoate dissolved in a pharmaceutically acceptable oil, or by orally administering such an oily solution.

The dose of and regimen of administration MENT undecanoate, or a pharmaceutical composition thereof, to be administered will obviously depend on the therapeutic effect to be achieved and will vary with the route of administration, and the age and condition of the individual subject to whom the medicament is to be administered, and/or or the particular contraceptive or HRT regimen in which it is used. Typical doses are 100 mg or more per three months upon intramuscular administration and 50–250 mg, more preferably 80 mg per day upon oral administration.

The invention will be further explained hereinafter with reference to the following Examples.

EXAMPLE 1

(7α,17β)-7-Methyl-17-[(1-oxoundecyl)oxy]estr-4-en-3-one

A total of 2.23 grams of commercially available undecanoyl chloride were added to a stirred solution of 1.58 grams of (7α,17β)-17-hydroxy-7-methylestr-4-en-3-one at 0–5° C. reaction mixture was allowed to reach room temperature and stirred overnight. Thereafter, ice was added and after stirring for another 2 hours the reaction mixture was poured into ice-water, containing 4 ml of conc. $H_2SO_4$, followed by ethyl acetate extraction. The organic layers were washed with water, cold 1 N NaOH solution and brine, dried on sodium sulfate, filtered and evaporated in vacuo. The residue was chromatographed over silica. Elution with heptane-ethylacetate (4:1) and evaporation gave a greasy solid that was collected. Yield 1.42 g, $[\alpha]_D^{20}$=+36° (c=1; dioxane), MS (ESI): 456.

(17β)-17-[(1-Oxoundecyl)oxy]androst-4-en-3-one

"Testosterone undecanoate" is commercially available.

EXAMPLE 2

About 20–30 mgs of compound were powdered and then dissolved in as little solvent as necessary to dissolve all the visible particles. Dissolution was accomplished by heating in a waterbath of 50° C. and shaking on a Vortex™ shaker for 15 minutes. The solubility was calculated by determining the amount of compound (in mg) dissolved per ml of solvent.

COMPARATIVE EXAMPLE

The solubility and the androgenic potency of the compound of the invention and three reference compounds was used to determine RDP. The results are given in the tables below. With regard to clinically desirable anabolic and antigonadotropic effects (androgenic effects), MENT is ten times more potent than testosterone in rats (Kumar N et al, Endocrinology 130: 3677–3683 (1992) and J Steroid Biochem Molec Biol 52: 105–112 (1995)) and monkeys (Cummings D et al, J Clin Endocrinol Metab 83, 4212–4219 (1998)). The RDP is determined as follows:

$$\frac{\text{Solubility of compound}}{\text{Solubility of testosterone}} \times \text{potency of compound relative to that of testosterone}$$

TABLE 1

| compound | solubility arachis oil | solubility oleic acid |
| --- | --- | --- |
| testosterone | <<0.1 mg/ml | ~25 mg/ml |
| MENT | ≦0.1 mg/ml | ~15 mg/ml |
| testosterone undecanoate | ~45 mg/ml | 200–250 mg/ml |
| MENT undecanoate | >200 mg/ml | >500 mg/ml |

From the table it can be learned that the solubility of MENT undecanoate in arachis oil is much better than that of any of the other androgens. The solubility of MENT undecanoate in oleic acid is also better than expected in view of that of the known androgens.

TABLE 2

| compound | RDP in arachis oil | RDP in oleic acid |
| --- | --- | --- |
| testosterone | 1 | 1 |
| MENT | 10 | 6 |
| testosterone undecanoate | 450 | 8–10 |
| MENT undecanoate | 20.000 | ≧200 |

What is claimed is:

1. The compound (7α,17β)-7-methyl-17-[(1-oxoundecyl)oxy]estr-4-en-3-one.

2. A pharmaceutical formulation comprising the compound of claim 1 and a pharmaceutically acceptable carrier.

3. The pharmaceutical formulation according to claim 2, wherein the carrier is a liquid.

4. A method for treating androgen insufficiencies in a patient, comprising:

administering to a patient an effective amount of the pharmaceutical formulation of claim 2.

5. The method according to claim 4, wherein the pharmaceutically acceptable carrier in the pharmaceutical formulation is a liquid.

6. The method according to claim 4, wherein administration is intramuscular administration in an amount of 100 mg or more per three months.

7. The method according to claim 4, wherein administration is oral administration in an amount of 50–250 mg per day.

* * * * *